United States Patent
Yoo

(12)
(10) Patent No.: US 9,254,119 B2
(45) Date of Patent: Feb. 9, 2016

(54) ULTRASOUND PROBE AND MANUFACTURING METHOD THEREOF

(71) Applicant: SAMSUNG MEDISON CO., LTD., Hongcheon-gun, Gangwon-do (KR)

(72) Inventor: Beom Keun Yoo, Incheon (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 59 days.

(21) Appl. No.: 14/161,401

(22) Filed: Jan. 22, 2014

(65) Prior Publication Data

US 2014/0358008 A1    Dec. 4, 2014

(30) Foreign Application Priority Data

May 30, 2013    (KR) .................. 10-2013-0061410

(51) Int. Cl.
*A61B 8/00* (2006.01)
*G10K 11/30* (2006.01)

(52) U.S. Cl.
CPC ............... *A61B 8/54* (2013.01); *A61B 8/4281* (2013.01); *A61B 8/4444* (2013.01); *G10K 11/30* (2013.01); *Y10T 29/49826* (2015.01)

(58) Field of Classification Search
CPC ........ A61B 8/12; A61B 8/483; A61B 8/0883; A61B 8/00
See application file for complete search history.

(56) References Cited

U.S. PATENT DOCUMENTS 8,702,612 B2 *   4/2014   Hendriks et al. .............. 600/466

FOREIGN PATENT DOCUMENTS

| EP | 1 816 492 A1 | 8/2007 |
|---|---|---|
| EP | 2 405 671 A1 | 1/2012 |
| WO | 2007/125500 A2 | 11/2007 |
| WO | 2008/084455 A1 | 7/2008 |

OTHER PUBLICATIONS

Extended European Search Report issued in European Application No. 14151364.8-1660 dated May 9, 2014.

* cited by examiner

*Primary Examiner* — Joel Lamprecht
(74) *Attorney, Agent, or Firm* — McDermott Will & Emery LLP

(57) ABSTRACT

Disclosed herein is an ultrasound probe which may adjust curvature of an acoustic lens using a shape memory alloy. The ultrasound probe includes an acoustic lens, a focus adjusting unit installed on the acoustic lens and deforming the shape of the acoustic lens to adjust the focus of ultrasonic waves radiated through the acoustic lens, and a current applying unit applying current to the focus adjusting unit to contract or expand the focus adjusting unit.

13 Claims, 7 Drawing Sheets

(a)

(b)

(c)

ULTRASOUND PROBE AND MANUFACTURING METHOD THEREOF

CROSS-REFERENCE TO RELATED APPLICATION

This application claims the benefit of Korean Patent Application No. 2013-0061410, filed on May 30, 2013 in the Korean Intellectual Property Office, the disclosure of which is incorporated herein by reference.

BACKGROUND

1. Field

Embodiments of the present invention relate to an ultrasound probe which generates images of the inside of an object using ultrasonic waves and a manufacturing method thereof.

2. Description of the Related Art

In general, an ultrasound diagnostic apparatus radiates an ultrasound signal to a target region of the inside of an object from the surface of the object, and non-invasively acquires tomographic images or images regarding a blood current of soft tissues using information of ultrasound signals (ultrasound echo signals) reflected by the target region.

As compared to other image diagnostic apparatuses, such as an X-ray diagnostic apparatus, a computed tomography (CT) scanner, a magnetic resonance imaging (MRI) apparatus, and a nuclear medicine diagnostic apparatus, the ultrasonic diagnostic apparatus is small and inexpensive, displays images in real time, and has high safety without X-ray exposure. Due to these advantages, the ultrasonic diagnostic apparatus is used for diagnosis of the heart, the abdomen, the renal system, and in obstetrics and gynecology.

The ultrasound diagnostic apparatus includes an ultrasound probe transmitting an ultrasound signal to an object and receiving ultrasound echo signals reflected by the object so as to acquire ultrasound images of the object.

The ultrasound probe includes a transducer in which a piezoelectric material vibrates and converts electrical signals and acoustic signals into each other, a matching layer reducing an acoustic impedance difference between the transducer and the object so as to maximally transmit ultrasonic waves generated from the transducer to the object, an acoustic lens focusing ultrasonic waves progressing in the forward direction of the transducer at a specific point, and a sound-absorbing layer blocking ultrasonic waves progressing in the backward direction of the transducer to prevent image distortion.

SUMMARY

Therefore, it is an aspect of the present invention to provide an ultrasound probe which may adjust curvature of an acoustic lens using a shape memory alloy and a manufacturing method thereof.

Additional aspects of the invention will be set forth in part in the description which follows and, in part, will be obvious from the description, or may be learned by practice of the invention.

In accordance with one aspect of the present invention, an ultrasonic probe includes an acoustic lens, a focus adjusting unit installed on the acoustic lens and deforming the shape of the acoustic lens to adjust the focus of ultrasonic waves radiated through the acoustic lens, and a current applying unit applying current to the focus adjusting unit to contract or expand the focus adjusting unit.

The focus adjusting unit may include at least one wire formed of a shape memory alloy.

The at least one wire may be attached to or inserted into the acoustic lens in the azimuthal direction.

The at least one wire may be attached to or inserted into the acoustic lens along the boundary of the acoustic lens.

The current applying unit may apply current to the at least one wire to contract or expand the at least one wire.

The focus adjusting unit may deform the shape of the acoustic lens to change curvature of the acoustic lens.

When current is applied to the focus adjusting unit from the current applying unit, the focus adjusting unit may contract and increase curvature of the acoustic lens.

The ultrasound probe may further include a current adjusting unit allowing a user to adjust current applied to the focus adjusting unit through the current applying unit.

In accordance with another aspect of the present invention, a manufacturing method of an ultrasound probe includes installing a focus adjusting unit, deforming the shape of an acoustic lens to adjust the focus of ultrasonic waves radiated through the acoustic lens, on the acoustic lens, and installing the acoustic lens provided with the focus adjusting unit on the front surface of a matching layer.

The focus adjusting unit may include at least one wire formed of a shape memory alloy.

The installation of the focus adjusting unit may include attaching or inserting the at least one wire to or into the acoustic lens in the azimuthal direction.

The installation of the focus adjusting unit may include attaching or inserting the at least one wire to or into the acoustic lens along the boundary of the acoustic lens.

In accordance with yet another aspect of the present invention, a control method of an ultrasound probe includes receiving a signal output from a current adjusting unit of the ultrasound probe corresponding to user operation, outputting a current applying signal corresponding to the signal output from the current adjusting unit to a current applying unit of the ultrasound probe, and causing the current applying unit to apply current to a focus adjusting unit of the ultrasound probe according to the current applying signal.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Figure 1:
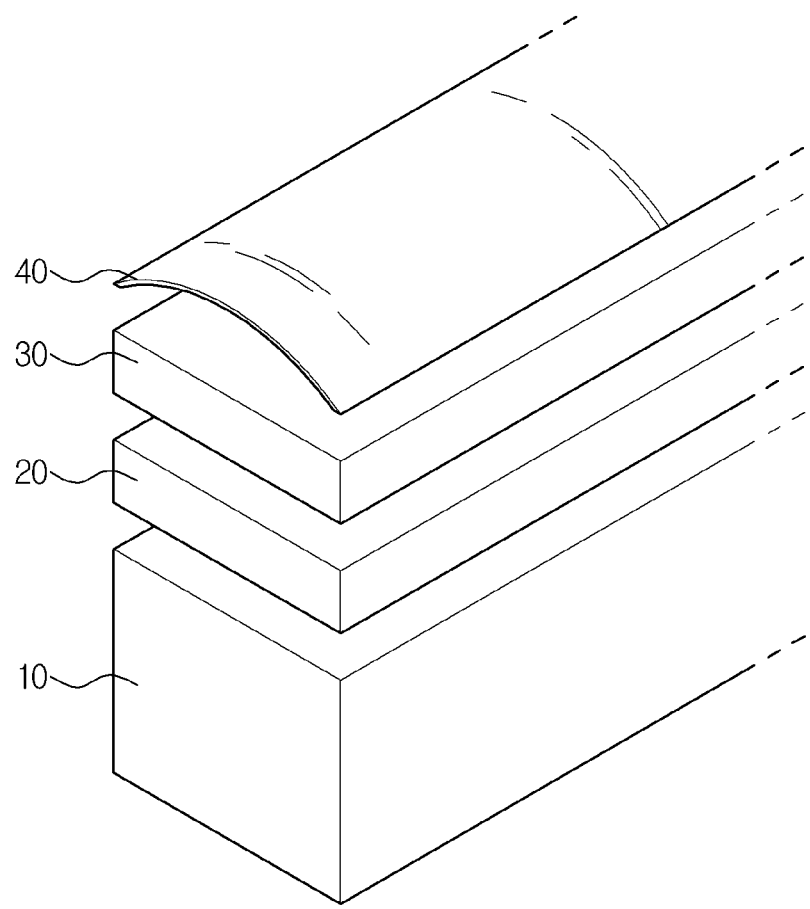
FIG. 1 is a view illustrating the structure of an ultrasound probe in accordance with one embodiment of the present invention.

Reference will now be made in detail to the embodiments of the present invention, examples of which are illustrated in the accompanying drawings, wherein like reference numerals refer to like elements throughout.

FIG. 1 is a view illustrating the structure of an ultrasound probe in accordance with one embodiment of the present invention.

With reference to FIG. 1, the ultrasound probe in accordance with this embodiment includes a sound-absorbing layer 10, a transducer 20 installed on the front surface of the sound-absorbing layer 10, a matching layer 30 installed on the front surface of the transducer 20, and an acoustic lens 40 installed on the front surface of the matching layer 30.

For example, as the transducer 20, a magnetostrictive ultrasound transducer using the magnetostrictive effect of a magnetic material, a capacitive micromachined ultrasound transducer transmitting and receiving ultrasonic waves using vibration of hundreds or thousands of micromachined films, or a piezoelectric ultrasound transducer using the piezoelectric effect of a piezoelectric material may be used. Hereinafter, a piezoelectric ultrasound transducer used as the transducer 20 will be exemplarily described.

When mechanical pressure is applied to a designated material, voltage is generated, and when voltage is applied, mechanical deformation of the material occurs. Such an effect is referred to as the piezoelectric effect or the inverse piezoelectric effect, and a material having such an effect is referred to as a piezoelectric material.

That is, a piezoelectric material is a material converting electrical energy into mechanical vibration energy or converting mechanical vibration energy into electrical energy.

The ultrasound probe in accordance with this embodiment of the present invention includes the transducer 20 formed of a piezoelectric material that, when an electrical signal is applied to the transducer 20, converts the electrical signal into mechanical vibration and thus generates ultrasonic waves.

The piezoelectric material of the transducer 20 may include ceramic of lead zirconate titanate (PZT), a PZMT single crystal formed of a solid solution of lead magnesium niobate and lead titanate, a PZNT single crystal formed of a solid solution of lead zinc niobate and lead titanate, PMN-PT, or a single crystal basically doped with PMN-PT.

Further, the transducer 20 may be arranged in a single layered structure or a multi-layered stack structure.

In general, the transducer 20 of a stack structure may more easily adjust impedance and voltage and thus acquire high sensitivity, high energy conversion efficiency, and a soft spectrum.

Further, electrodes to which electrical signals may be applied may be formed on the front and rear surfaces of the transducer 20. If electrodes are formed on the front and rear surfaces of the transducer 20, one of the electrodes formed on the front and rear surfaces of the transducer 20 may be a ground electrode and the other may be a signal electrode.

The matching layer 30 may be installed on the front surface of the transducer 20. The matching layer 20 reduces an acoustic impedance difference between the transducer 30 and an object and thus matches the acoustic impedances of the transducer 30 and the object, thereby effectively transmitting ultrasonic waves generated from the transducer 20 to the object.

For this purpose, the matching layer 30 may be provided so as to have a median value between the acoustic impedance of the transducer 20 and the acoustic impedance of the object.

The matching layer 30 may be formed of carbon, glass, or a resin.

Further, the matching layer 30 may include a plurality of matching layers 30 so that acoustic impedance may be changed in stages from the transducer 20 to the object, and the plural matching layers 30 may be formed of different materials.

The transducer 20 and the matching layer 30 may be processed to a matrix-type 2D array through a dicing process, or be processed to a 1D array.

Although shown in the drawings, a protective layer may be installed on the front surface of the matching layer 30, and the acoustic lens 40 may be installed on the front surface of the protective layer. The protective layer may include an RF shield to prevent a high frequency component which may be generated from the transducer 20 from leaking to the outside and to block introduction of high frequency signals from the outside. Further, the protective layer may include a chemical shield formed by coating or depositing a conductive material on the surface of a moisture and chemical resistant film to protect inner part from water or chemicals used for disinfection.

In order to focus ultrasonic waves, the acoustic lens 40 may be formed in a convex shape in the radiation direction of the ultrasonic waves, or be formed in a concave shape if sound velocity is lower than in a human body. The acoustic lens 40 in accordance with this embodiment may be formed of an elastic material which is changeable in shape, scarcely cause fatigue due to deformation, and returns to its original shape prior to deformation.

Figure 2A:
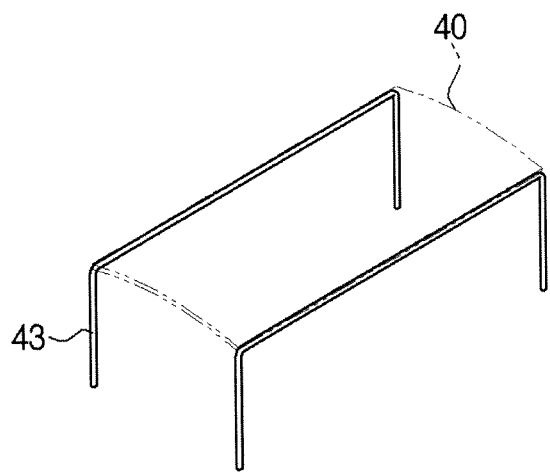
FIGS. 2(a) to 2(c) are views illustrating various examples of a focus adjusting unit installed on an acoustic lens in accordance with the embodiment of the present invention.
Figure 2B:
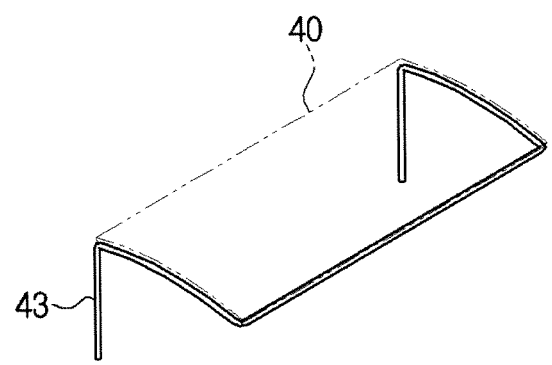
Figure 2C:
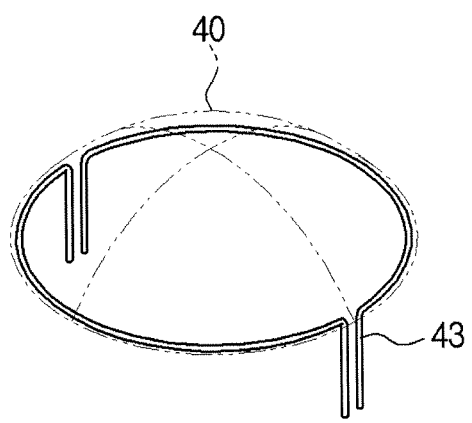

The acoustic lens 40 of the ultrasound probe in accordance with this embodiment of the present invention includes a focus adjusting unit 43 changing the shape of the acoustic lens 40 to change the focus of ultrasonic waves radiated through the acoustic lens 40. FIGS. 2(a) to 2(c) are views illustrating various examples of the focus adjusting unit 43 installed on the acoustic lens 40 in accordance with the embodiment of the present invention.

As exemplarily shown in FIGS. 2(a) to 2(c), the focus adjusting unit 43 may be attached to or inserted into the boundary of the acoustic lens 40. The focus adjusting unit 43 shown in FIG. 2(a) or 2(b) may be installed on the acoustic lens 40 having the same shape as the acoustic lens 40 exemplarily shown in FIG. 1. That is, the focus adjusting unit 43 may be installed along the boundary of the acoustic lens 40.

If the acoustic lens 40 has the shape shown in FIG. 2(c), the focus adjusting unit 43 may be installed at the boundary of the acoustic lens 40 in the azimuthal direction.

Further, the focus adjusting unit 43 may be formed in the type of a wire, a coil, or a frame formed of a shape memory alloy. For example, as exemplarily shown in FIGS. 2(a) to 2(c), the focus adjusting unit 43 may be formed as a wire which may be easily processed.

Since the focus adjusting unit 43 is formed of a shape memory alloy, when current is applied to the focus adjusting unit 43, the focus adjusting unit 43 contracts. Since the focus adjusting unit 43 is installed on the acoustic lens 40, when the focus adjusting unit 43 contracts, the convex portion of the lens 40 contracts and curvature of the acoustic lens 40 is increased, and when curvature of the acoustic lens 40 is increased, a focusing distance of the ultrasound probe with respect to ultrasonic waves is shortened.

When the curvature of the acoustic lens 40 is changed, as describe above, a space may be formed between the acoustic lens 40 and the matching layer 30 or an existing space may be expanded. In the ultrasound probe in accordance with the embodiment of the present invention, the space between the acoustic lens 40 and the matching layer 30 varying according to change of the curvature of the acoustic lens 40 may be filled with a liquid. By filling the vacant space with a liquid, radiation of ultrasonic waves may be more effectively carried out.

Change of the curvature of the acoustic lens 40 may be adjusted by adjusting the intensity of current applied to the focus adjusting unit 43, and therethrough, the focusing distance of the ultrasound probe with respect to ultrasonic waves may be adjusted.

By changing the curvature of the acoustic lens 40 using the focus adjusting unit 43 formed of a shape memory alloy, as described above, the focusing distance may be variously changed using only one ultrasound probe without replacement of the ultrasonic probe.

Figure 3:
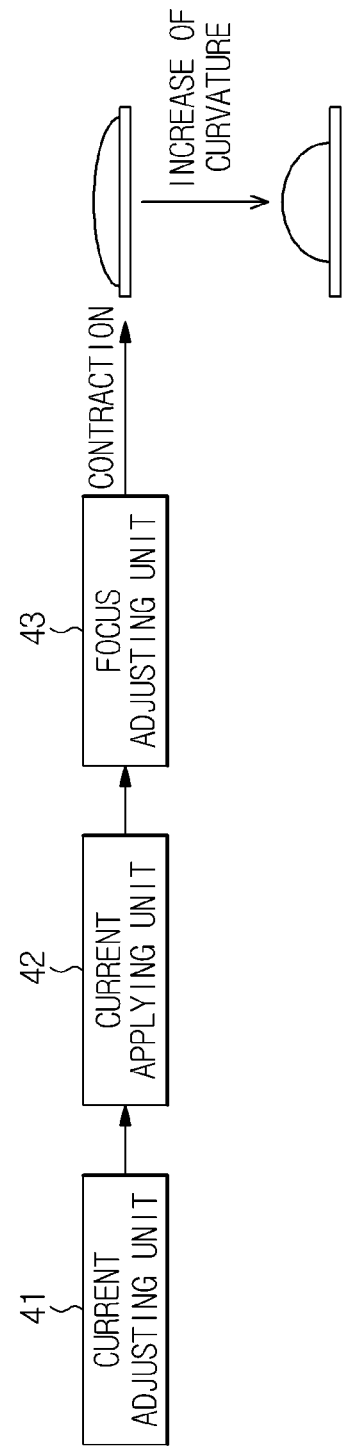
FIG. 3 is a block diagram illustrating a configuration to control curvature of the acoustic lens in accordance with the embodiment of the present invention.
Figure 4:
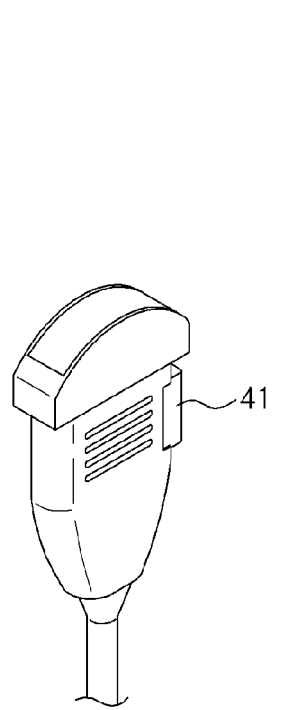
FIGS. 4(a) to 4(c) are views illustrating various examples of a current adjusting unit of the ultrasound probe in accordance with the embodiment of the present invention.
Figure 4:
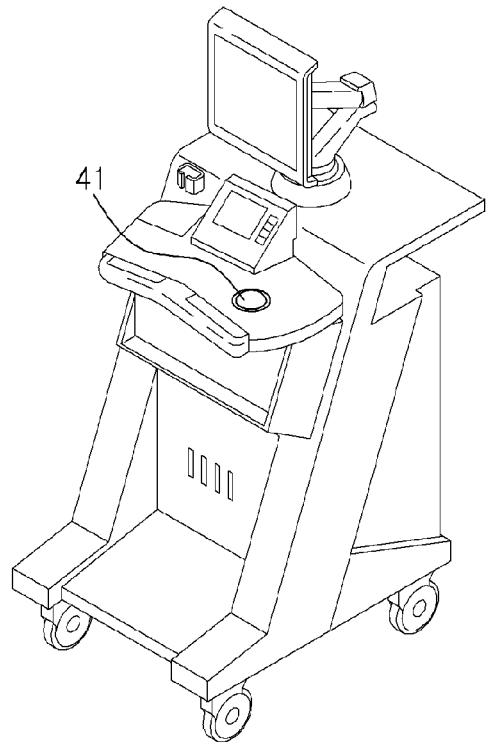
Figure 4:
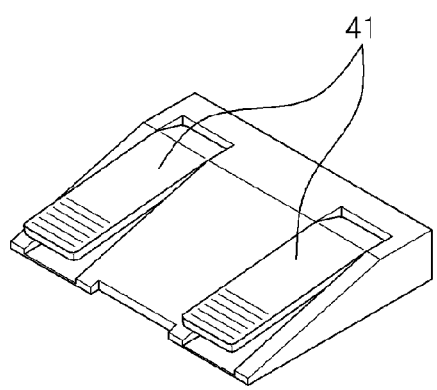

FIG. 3 is a block diagram illustrating a configuration to control curvature of the acoustic lens 40, and FIGS. 4(*a*) to 4(*c*) are views illustrating various examples of a current adjusting unit 41 of FIG. 3.

The ultrasound probe in accordance with the embodiment of the present invention further includes a current applying unit 42 applying current to the above-described focus adjusting unit 43, and a current adjusting unit 41 allowing a user to apply current to the focus adjusting unit 43 to adjust the focusing distance of the ultrasound probe.

The current adjusting unit 41 is provided on the ultrasound probe so that the user may adjust the focusing distance of the ultrasound probe with respect to ultrasonic waves radiated through the acoustic lens 40.

A button-type current adjusting unit 41 may be provided on the outer surface of the ultrasound probe, as exemplarily shown in FIG. 4(*a*), or a dial-type toggle switch serving as the current adjusting unit 41 may be provided on a panel of a rear end apparatus to control the overall operation of the ultrasonic probe, as exemplarily shown in FIG. 4(*b*). Otherwise, a pedal-type current adjusting unit 41 may be provided, as exemplarily shown in FIG. 4(*c*). The current adjusting units 41 exemplarily shown in FIGS. 4(*a*) to 4(*c*) are just examples, and the embodiments of the present invention are not limited thereto. When a user operates the current adjusting unit 41, the focusing distance of the ultrasound probe which varies according to user operation may be displayed through a display of a rear end apparatus.

In order to change the focusing distance as desired by the user, the user may operate one of the current adjusting units 41, as exemplarily shown in FIGS. 4(*a*) to 4(*c*). When the user operates the current adjusting unit 41, the current adjusting unit 41 generates a current applying signal corresponding to user operation and outputs the current applying signal to the current applying unit 42.

The current applying unit 42 receives the current applying signal output from the current adjusting unit 41 and applies current corresponding to the current applying signal to the focus adjusting unit 43. The current applying unit 42 may include a power source generating electricity corresponding to the current applying signal applied from the current adjusting unit 41.

When current is supplied from the current applying unit 42 to the focus adjusting unit 43 formed of a shape memory alloy, the shape of the focus adjusting unit 43 is changed and thus the curvature of the acoustic lens 40 is changed. When current is applied from the current applying unit 42 to the focus adjusting unit 43 and thus the focus adjusting unit 43 contracts, the curvature of the acoustic lens 40 is increased and the focusing distance of the ultrasound probe with respect to ultrasonic waves is shortened.

Figure 5:
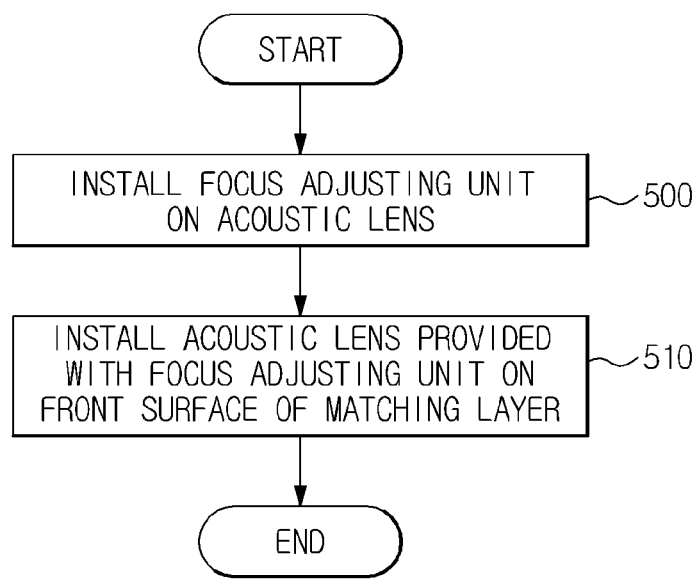
FIG. 5 is a flowchart illustrating a manufacturing method of an ultrasound probe in accordance with one embodiment of the present invention.

FIG. 5 is a flowchart illustrating a manufacturing method of an ultrasound probe in accordance with one embodiment of the present invention.

With reference to FIG. 5, the focus adjusting unit 43 is installed on the acoustic lens 40 (Operation 500).

The acoustic lens 40 of the ultrasound probe in accordance with the embodiment of the present invention includes the focus adjusting unit 43 changing the shape of the acoustic lens 40 to change the focus of ultrasonic waves radiated through the acoustic lens 40. FIGS. 2(*a*) to 2(*c*) illustrate various examples of the focus adjusting unit 43 installed on the acoustic lens 40 in accordance with the embodiment of the present invention.

As exemplarily shown in FIGS. 2(*a*) to 2(*c*), the focus adjusting unit 43 may be attached to or inserted into the boundary of the acoustic lens 40. The focus adjusting unit 43 shown in FIG. 2(*a*) or 2(*b*) may be installed on the acoustic lens 40 having the same shape as the shape exemplarily shown in FIG. 1. That is, the focus adjusting unit 43 may be installed along the boundary of the acoustic lens 40. If the acoustic lens 40 has the shape shown in FIG. 2(*c*), the focus adjusting unit 43 may be installed at the boundary of the acoustic lens 40 in the azimuthal direction.

Further, the focus adjusting unit 43 may be formed in the type of a wire, a coil, or a frame formed of a shape memory alloy. For example, as exemplarily shown in FIGS. 2(*a*) to 2(*c*), the focus adjusting unit 43 may be formed as a wire which may be easily processed.

Since the focus adjusting unit 43 is formed of a shape memory alloy, when current is applied to the focus adjusting unit 43, the focus adjusting unit 43 contracts. Since the focus adjusting unit 43 is installed on the acoustic lens 40, when the focus adjusting unit 43 contracts, the convex portion of the lens 40 contracts and curvature of the acoustic lens 40 is increased, and when curvature of the acoustic lens 40 is increased, a focusing distance of the ultrasound probe with respect to ultrasonic waves is shortened.

Change of the curvature of the acoustic lens 40 may be adjusted by adjusting the intensity of current applied to the focus adjusting unit 43, and therethrough, the focusing distance of the ultrasound probe with respect to ultrasonic waves may be adjusted.

When the focus adjusting unit 43 is installed on the acoustic lens 40, the acoustic lens 40 provided with the focus adjusting unit 43 is installed on the front surface of the matching layer 30 (Operation 510).

The matching layer 30 may be installed on the front surface of the transducer 20, and the acoustic lens 40 provided with the focus adjusting unit 43 may be installed on the front surface of the matching layer 30. Otherwise, the protective layer may be installed on the front surface of the matching layer 30, and the acoustic lens 40 may be installed on the front surface of the protective layer.

As is apparent from the above description, in an ultrasound probe and a manufacturing method thereof in accordance with one embodiment of the present invention, curvature of an acoustic lens may be adjusted.

Further, the focusing distance of the ultrasound probe may be changed by adjusting the curvature of the acoustic lens and, thus, accurate information of an object may be confirmed using only one ultrasonic probe.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:
1. An ultrasound probe comprising:
   an acoustic lens;
   a focus adjusting unit installed on the acoustic lens and deforming the shape of the acoustic lens to adjust the focus of ultrasonic waves radiated through the acoustic lens; and a current applying unit applying current to the focus adjusting unit to contract or expand the focus adjusting unit.

2. The ultrasound probe according to claim 1, wherein the focus adjusting unit includes at least one wire formed of a shape memory alloy.

3. The ultrasound probe according to claim 2, wherein the at least one wire is attached to or inserted into the acoustic lens in the azimuthal direction.

4. The ultrasound probe according to claim 2, wherein the at least one wire is attached to or inserted into the acoustic lens along the boundary of the acoustic lens.

5. The ultrasound probe according to claim 2, wherein the current applying unit applies current to the at least one wire to contract or expand the at least one wire.

6. The ultrasound probe according to claim 1, wherein the focus adjusting unit deforms the shape of the acoustic lens to change curvature of the acoustic lens.

7. The ultrasound probe according to claim 1, wherein, when current is applied to the focus adjusting unit from the current applying unit, the focus adjusting unit contracts and increases curvature of the acoustic lens.

8. The ultrasound probe according to claim 1, further comprising a current adjusting unit allowing a user to adjust current applied to the focus adjusting unit through the current applying unit.

9. A manufacturing method of an ultrasound probe comprising:

installing a focus adjusting unit, deforming the shape of an acoustic lens to adjust the focus of ultrasonic waves radiated through the acoustic lens, on the acoustic lens; and installing the acoustic lens provided with the focus adjusting unit on the front surface of a matching layer.

10. The manufacturing method according to claim 9, wherein the focus adjusting unit includes at least one wire formed of a shape memory alloy.

11. The manufacturing method according to claim 10, wherein the installation of the focus adjusting unit includes attaching or inserting the at least one wire to or into the acoustic lens in the azimuthal direction.

12. The manufacturing method according to claim 10, wherein the installation of the focus adjusting unit includes attaching or inserting the at least one wire to or into the acoustic lens along the boundary of the acoustic lens.

13. A control method of an ultrasound probe comprising:

receiving a signal output from a current adjusting unit of the ultrasound probe corresponding to user operation;

outputting a current applying signal corresponding to the signal output from the current adjusting unit to a current applying unit of the ultrasound probe; and causing the current applying unit to apply current to a focus adjusting unit of the ultrasound probe according to the current applying signal.

\* \* \* \* \*